United States Patent [19]

Lustig

[11] 4,268,252

[45] May 19, 1981

[54] CONTRA-ANGLE HEAD FOR DENTISTRY

[76] Inventor: Leopold P. Lustig, 304 Greenwood St., Newton Centre, Mass. 02159

[21] Appl. No.: 75,013

[22] Filed: Sep. 13, 1979

[51] Int. Cl.³ .............................................. A61C 1/14
[52] U.S. Cl. .................................... 433/128; 433/126; 433/116; 433/133
[58] Field of Search ............... 433/127, 126, 128, 116, 433/133, 125, 105, 128

[56] References Cited

U.S. PATENT DOCUMENTS

| | | | |
|---|---|---|---|
| 684,951 | 10/1901 | Rothkranz | 433/116 |
| 886,862 | 5/1908 | Repsold | 433/116 |
| 1,042,039 | 10/1912 | Schlund | 433/116 |
| 1,380,717 | 6/1921 | Herman | 433/125 |
| 1,497,561 | 6/1924 | Gruss | 433/116 |
| 1,691,823 | 11/1928 | Ogilvie | 433/116 |
| 2,202,299 | 5/1940 | Pelkey | 433/133 |
| 2,319,328 | 5/1943 | Kaltenbach | 433/116 |
| 2,591,772 | 4/1952 | Bjorklund | 433/133 |
| 2,752,682 | 7/1956 | Wiseman | 433/127 |
| 2,894,325 | 7/1959 | Flatland | 433/128 |
| 3,798,777 | 3/1974 | Reiter | 433/133 |
| 4,053,983 | 10/1977 | Flatland | 433/133 |

FOREIGN PATENT DOCUMENTS

| | | | |
|---|---|---|---|
| 525670 | 5/1931 | Fed. Rep. of Germany | 433/126 |
| 626591 | 9/1927 | France | 433/127 |
| 11870 | 7/1902 | United Kingdom | 433/133 |

*Primary Examiner*—Gene Mancene
*Assistant Examiner*—John J. Wilson
*Attorney, Agent, or Firm*—Alfred H. Rosen

[57] ABSTRACT

A rigid tubular housing provides separate enclosures for a drive shaft and a dental tool that are rotatable on axes that are angularly related. A wall separating the two enclosures provides bearing support for tool-driving gears in one of the enclosures and connection to a driving shaft in the other. A latching mechanism envelops the housing and covers it smoothly. The latching mechanism is movable on the longitudinal axis of the tubular housing for controlling access to the enclosure for a dental tool.

8 Claims, 16 Drawing Figures

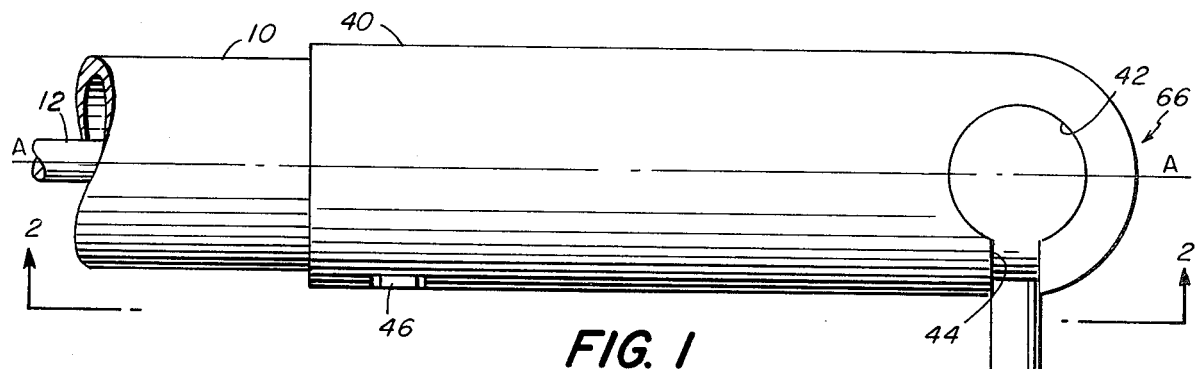
FIG. 1
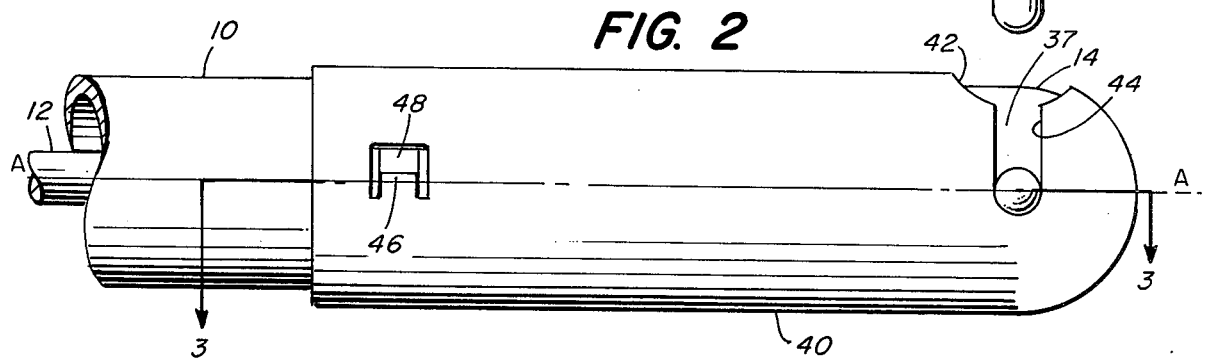
FIG. 2
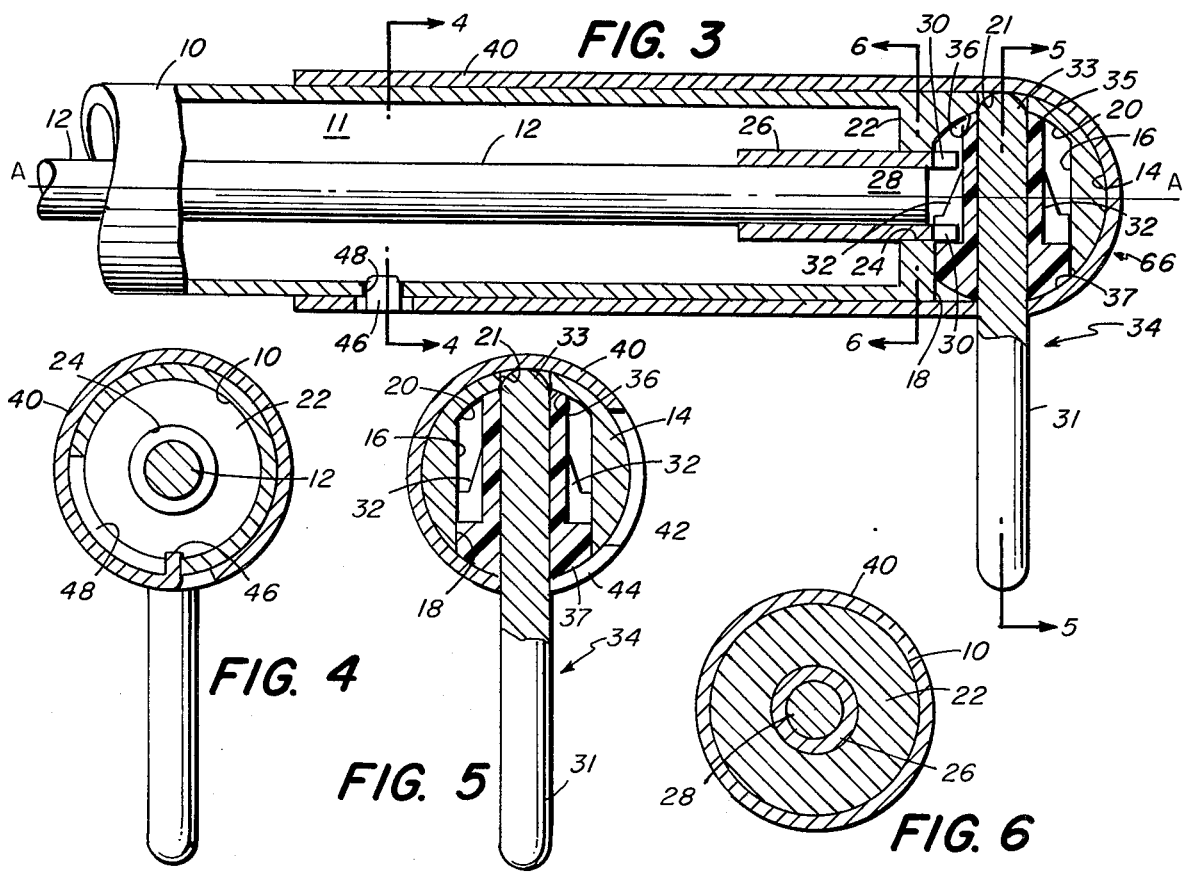
FIG. 3
FIG. 4
FIG. 5
FIG. 6

CONTRA-ANGLE HEAD FOR DENTISTRY

BACKGROUND OF THE INVENTION

Contra-angle heads for use in dentistry, as presently known in the art, have become highly developed for both general and specific purposes. Examples, taken at random, are described in U.S. Pat. Nos. 3,369,298; 3,578,745; and 4,053,983; which are directed respectively to a clutch mechanism, an oscillating broach for endodontic work, and a prophylactic head for a dental handpiece. These examples illustrate, in a limited way, the variety of applications existing for contra-angle heads, and the variety of structures which have evolved in response to them.

Those contra-angle heads intended for use by a dentist to drive interchangeably one or more of drills, burs, broaches, files and other tools used in dentistry incorporate rugged and usually precise mechanisms for accepting and locking the tools in place, driving them at desired speeds, and releasing them for removal, quickly and reliably, but for the most part such contra-angle heads are bulky and large, have awkward shapes, and are heavy. The positions into which a dentist can put a tool in the mouth of a patient are restricted, and often a tool can be used to treat a patient only at the expense of great discomfort to the patient, and risk of harming surrounding tissue that is not directly involved in the procedure being undertaken.

Projecting parts, such as extending gear boxes and external latching levers, which are commonly found on contra-angle heads currently in use tend to aggravate such discomfort and risks. For example, in U.S. Pat. No. 3,369,298 a clutch is permanently rotatably fixed in a stub-housing oriented transverse to the principal housing, and gears to rotate the clutch on an axis transverse to the main drive shaft axis are housed in the stub housing, which is enlarged for that purpose. A tool can be removably inserted into the clutch from one end of the stub housing, and a lock lever is provided, externally, at the other end.

Attempts to provide smaller and smoother contra-angle heads with interchangeable tools have lead, in one instance, to a construction in which the tool is inserted through the stub housing from the locking end, and a threaded cap is provided at the same end to perform the locking function. As it is attempted to make a contra-angle head smaller, these parts, especially removable caps, become so small that they are easily lost, wasting the time of the dentist, and so expensive that their prices are difficult to justify in times of rising prices of other more important medical procedures.

GENERAL NATURE OF THE INVENTION

With this invention I provide a new contra-angle head that is rugged, safe and convenient to use, has a convenient latch mechanism which is devoid entirely of projections and extensions and which has a smooth outer surface surrounding the entire end of the head that is put into the mouth of a patient, can be made without angular contours, and while providing ready interchangeability of tools can be made smaller in size than prior contra-angle heads having similar operating features. My new contra-angle head can be used with a limitless variety of tools, as well as for prophylactic devices.

In my new contra-angle head, a rigid tubular housing, which can be made in one piece of any suitable material, such as metal or plastic, provides in one body elongated on the tubular axis two separate enclosures, one being an alley for a drive shaft and the other being a chamber for a dental tool, respectively, which rotate on axes that are angularly related, A comparatively massive wall separates the shaft alley from the tool chamber, and has an aperture communicating with both enclosures. This wall supplies bearing support for a drive shaft extending into the tool chamber from the shaft alley, or for a stub shaft communicating with both enclosures. Either shaft supports tool-driving gears in the tool chamber, which has an opening through a side wall of the housing for passage of a tool being installed or removed. A tubular latch member closely envelopes substantially the entire housing, including the end enclosing the tool chamber, with a thin-walled cover having a smooth outer surface that is entirely devoid of projections, extensions, and angular surfaces. This latch mechanism is movable on the tubular axis relative to the housing, either circumferentially, or longitudinally (ie: "telescopically") to latch or unlatch a tool in the tool chamber. Some embodiments of the invention will now be described with reference to the accompanying drawings.

BRIEF DESCRIPTION OF THE DRAWINGS

FIG. 1 is a side view of a contra-angle head according to the invention;

FIG. 2 is a bottom view of the contra-angle head from line 2—2 in FIG. 1;

FIG. 3 is a partial longitudinal section on line 3—3 of FIG. 2;

FIG. 4 is a cross-section on line 4—4 of FIG. 2;

FIG. 5 is a cross-section on line 5—5 of FIG. 2;

FIG. 6 is a cross-section on line 6—6 of FIG. 2;

DETAILED DESCRIPTION OF THE DRAWINGS

Figure 5A:
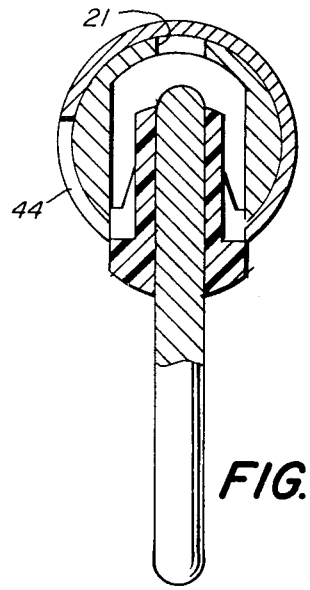
FIG. 5A is a view of FIG. 5 with an outer locking member moved into an unlocking position, showing the tool member partly withdrawn.
Figure 11:
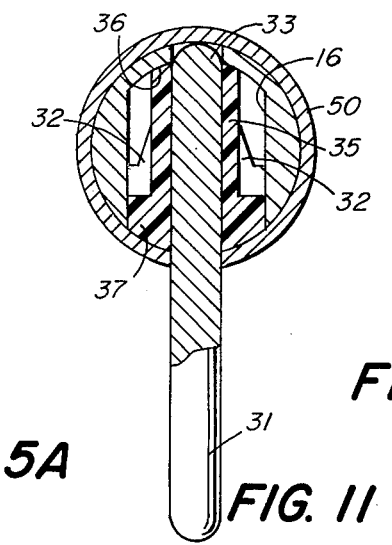
FIG. 11 is a cross-section taken on line 11—11 of FIG. 8.
Figure 10:
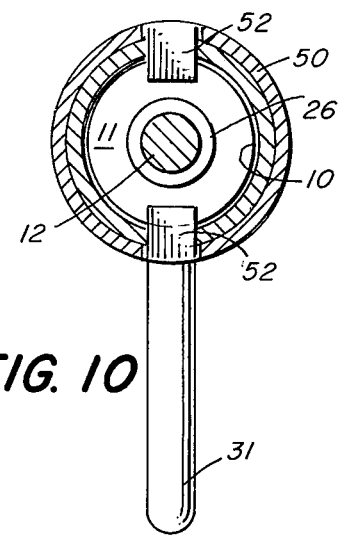
FIG. 10 is a cross-section taken on line 10—10 of FIG. 8.

In FIGS. 1–6, inclusive, a principal tubular housing 10 provides a shaft alley 11 for enclosing a drive shaft 12 which is rotatable around the longitudinal axis A—A of the housing. The housing 10 has one end 14 rounded on the outside transversely to the axis A—A, and fitted with a tool chamber 16 having an opening 18 into the housing at one side and extending from that opening transversely to the axis A—A toward the opposite side of the housing where it terminates in a dome-like interior wall 20, with an aperture 21 through it (FIGS. 3,5). A transverse wall 22 between the tool chamber 16 and the shaft alley 11 has an aperture 24 on the axis to provide bearing support for the shaft 12 (FIG. 3). A coupling member 26 is fitted over the end 28 of the shaft and into the aperture 24. The coupling member has driving gear teeth 30 projecting into the tool chamber beyond the shaft end 28, for engaging the mating gear teeth 32 of a tool member 34 when the latter is present in the tool chamber, as shown in the drawings. In practice the contra-angle head will be fitted at the left-hand end of the housing 10 (as seen in the drawings) with means to couple it to a hand piece, of which several varieties are now in professional use. Such coupling means are not part of the invention, and are not illustrated. It will be understood that the shaft 12 is intended to be driven from the handpiece to which the contra-angle head is coupled.

The tool member 34 is similar to the dental tool (30) which is described and claimed in the co-pending U.S. Application Ser. No. 970,468 filed Dec. 18, 1978 by the present inventor and another. Like the tool (30) described in the referenced copending application, the gear teeth 32 of the present tool member 34 are particularly adapted to engage with the driving gear teeth 30 when the tool member is pushed into the tool chamber 16 and to disengage from the driving gear teeth 30 when the tool member is withdrawn from the tool chamber, as is illustrated in and will be described with reference to FIG. 5A. The tool shaft 31 has a rounded end 33 extending into the aperture 21 in the interior wall 20, when the tool is fully seated in the tool chamber.

An outer locking member 40 is coaxially fitted over the principal housing 10, covering the major portion of the principal housing axially and smoothly embracing the rounded end 14 of it. This essentially smooth covering for the entire "nose" end 66 of the contra-angle head is sanitary and safe to use; it has no projecting parts which could damage tissue in the mouth of a patient. The locking member has a round hole 42 through it from which a slot 44 extends a fixed distance circumferentially around the longitudinal axis A—A. This locking member 40 is rotatable circumferentially around the axis A—A, between limits set by a stop tab 46 bent radially inward from the locking member and engaged in a circumferential slot 48 in the principal housing 10, extending essentially one-quarter turn (90 degrees) around the axis A—A, as is best seen in FIG. 4. When the locking member is in the locked position shown in FIGS. 1–4, inclusive, the slot 44 overlies the opening 18 into the tool chamber, and if a tool member 34 is present, it is retained in place, as is best shown in FIGS. 3 and 5. The slot 44 has a width sufficient to let the shaft 31 of the tool member rotate in it. The tool member is fitted with a gear hub 35 (which may be made of a molded plastic or a sintered metal material, for example) having rounded end surfaces 36, 37 generally conforming, respectively, to the surface of the dome-like interior wall 20 of the tool chamber and the inner surface of the locking member. The rounded end 33 of the tool shaft extends through the aperture 21, to provide bearing support for the inner end of the tool shaft 31.

When the locking member 40 is moved to the unlocked position, which is done by rotating the locking member one-quarter turn clockwise around the axis A—A, as viewed in FIG. 4, the round hole 42 comes into register with the entrance 18 to the tool chamber, and a tool member 34 can be withdrawn or installed by moving it transversely to the longitudinal axis A—A, as FIG. 5A shows.

FIGS. 7 to 11, inclusive, show a second version of the invention, in which an axially-movable locking member 50 is substituted on the principal housing 10 for the circumferentially-movable locking member 40 of the version shown in FIGS. 1–6, inclusive. The operating principles are the same in both versions, and only the structural differences will be described.

Figure 8:
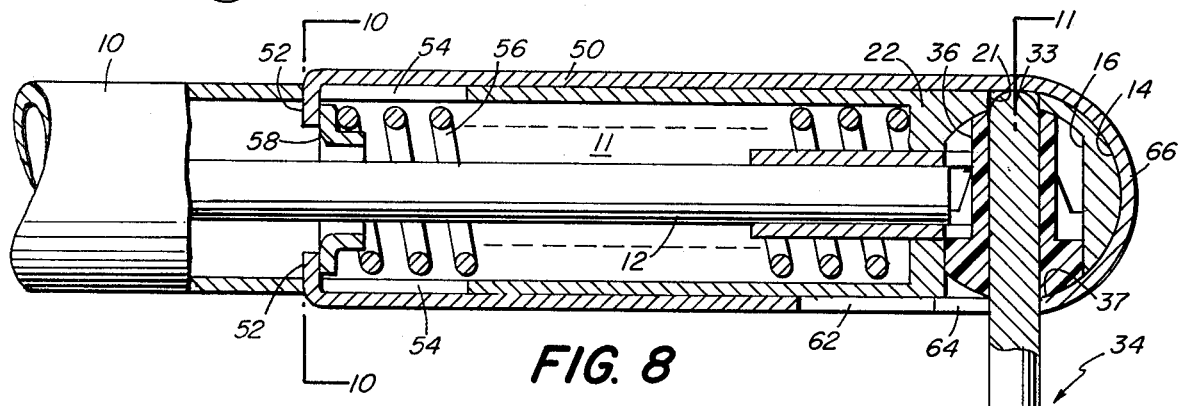
FIG. 8 is a partial longitudinal section on line 8—8 of FIG. 7.
Figure 8A:
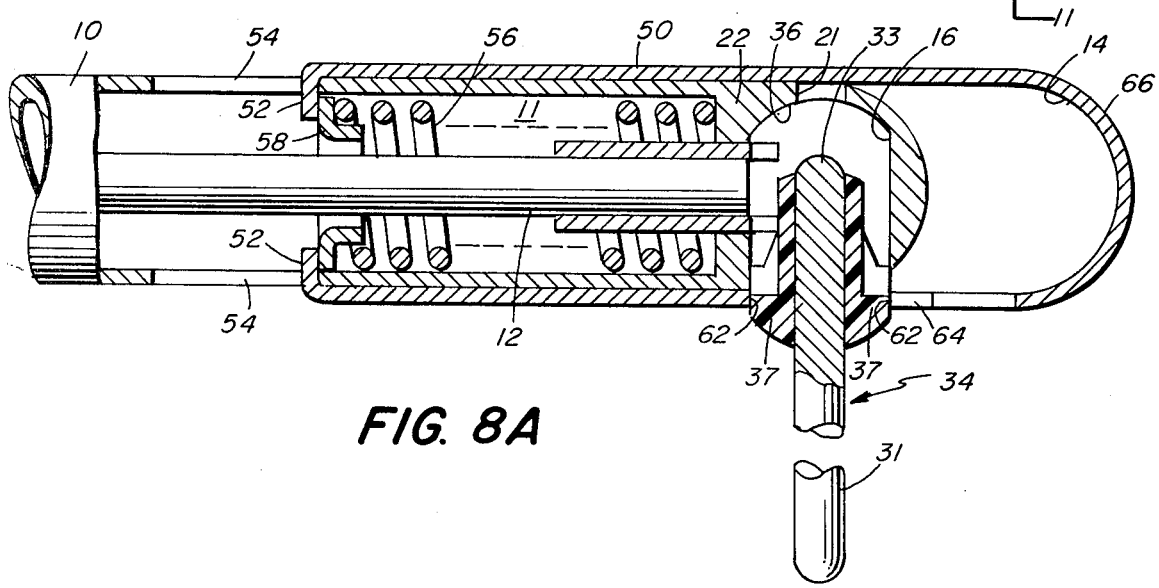
FIG. 8A is a view of FIG. 8 with an outer locking member moved into an unlocking position, showing the tool member partly withdrawn.
Figure 7:
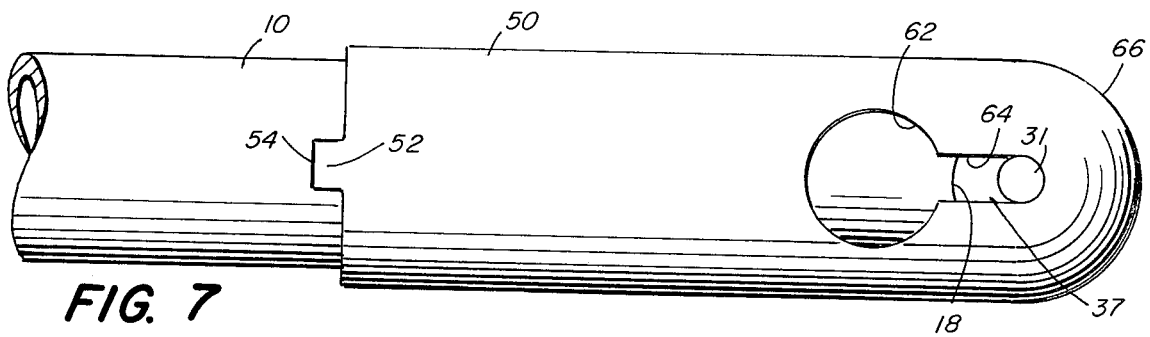
FIG. 7 is a bottom view, similar to FIG. 2, of another embodiment of the invention.
Figure 9:
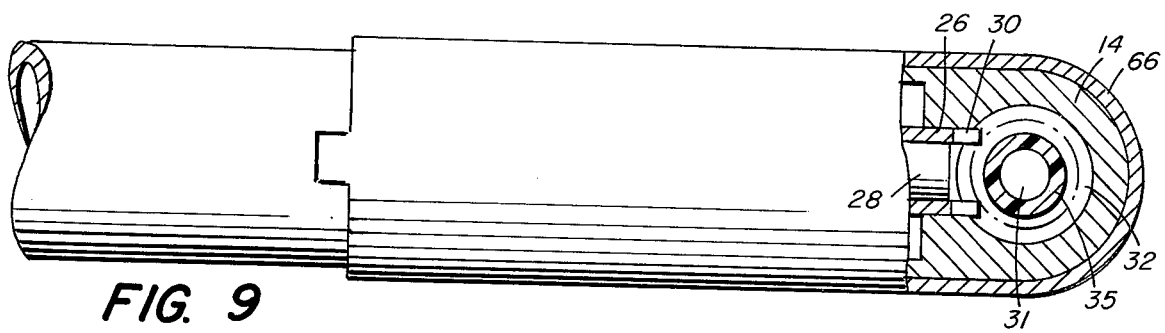
FIG. 9 is a fragmentary longitudinal section of a top view taken on line 9—9 of FIG. 8.

The locking member 50 has a pair of diametrically opposed limit tabs 52 extending radially inward, toward each other, in respective longitudinal slots 54 that are provided for them in the walls of the principal housing 10. These slots establish the limits of axial motion of the locking member. A round hole 62 from which a slot 64 extends in the axial direction toward the free end 66 is provided in the locking member, near the free end. A coaxial coil spring 56 is retained between a flanged washer 58 abutting the tabs 52 at one end, and the transverse wall 22 at the other. The coil spring urges the locking member to the locked position, shown in FIGS. 7 and 8, for example, in which the outer end 66 embraces the curved end 14 of the principal housing, and the slot 64 overlies the opening 18 into the tool chamber. When the locking member is moved axially against the force of the coil spring 56 (to the right, in the views shown in FIGS. 7, 8 and 9) so that the tabs 52 approach the right-hand ends of the slots 54, the round hole will overlie the opening into the tool chamber, and a tool member 34 can then be exchanged by moving it transversely to the longitudinal axis A—A, as is shown in FIG. 8A.

Figure 12:
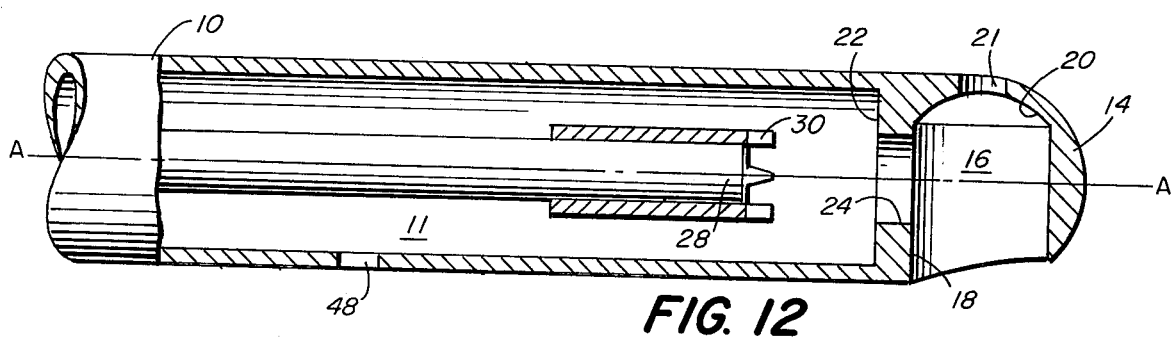
FIG. 12 is a partial longitudinal sectional and partially-exploded view of the contra-angle head shown in FIG. 1.

The housing 10 can be made as rigid as desired, and provides the basic foundation, or principal housing, for the contra-angle head. As has been noted, this housing can be made to fit any style or design of hand-piece that is or may be in use. Some handpieces are designed to retain the drive shaft 12 permanently fixed to the handpiece, in which case the housing 10 is capable of being separated from the drive shaft 12 when the contra-angle head is removed from a handpiece, as FIG. 12 illustrates. The transverse wall 22 defining the bearing aperture 24 is thick relative to other walls of the housing 10, and provides full support for the free end 28 of the shaft 12 and the coupling member 26 when the contra-angle head is installed on such a handpiece. For that reason, the shaft 12 can be made thinner than would be required if no bearing support were provided at its free end, and the designer is more free to choose a composite shaft in which torsional rigidity is the major concern. For example, a cable-like shaft, made of thin wires or fibers twisted around the axis A—A, can be used notwithstanding that it might be more flexible than a solid shaft in directions transverse to the longitudinal axis A—A.

Figure 13:
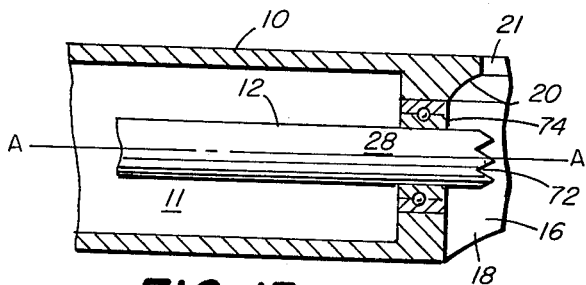
FIG. 13 is a fractional longitudinal sectional view of a variation of the invention.

The bearing space 24 can be fitted with an antifriction bearing 74, as is shown in FIG. 13, in which case the shaft 12 can be formed with drive gears 72 directly on its free end 28. The shaft 12 with gears 72 can be fixed in the housing 10, or removable according to FIG. 12.

Figure 14:
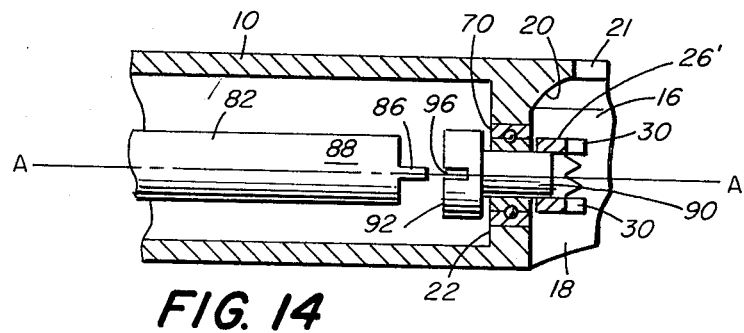
FIG. 14 is a fractional longitudinal sectional view of another variation of the invention.

In FIG. 14, the shaft 82 is fixed to the handpiece (not shown) and fitted at its free end 88 with a clutch member 86. THe driving gear teeth 30 are on a short coupling member 26' (similar to the coupling member 26 in FIG. 3, for example) fixed on a stub shaft 90 that is supported in the anti-friction bearing 70, through the transverse wall 22. On the side of the wall 22 opposite the driving gear teeth, the stub shaft 90 has a head 92 fitted with a slot 96 for engagement by the clutch member 86 when the contra-angle head is fully installed on an appropriate handpiece. The clutch member 86 and slot 96 are representative of any suitable mechanism for engaging the drive shaft 82 with the stub shaft 90 when the contra-angle head is installed, and for disengaging those shafts when the head is removed from a handpiece. FIG. 14 illustrates that group of embodiments of the invention in which the driving gears 30 or the like for a tool member are permanently installed in the principal housing 10 as an entity apart from the main drive shaft.

The tool chamber 16 may also be fitted with anti-friction bearing means for tool members, if desired. Embodiments of the invention which include such obvious structural details are intended to be included within the scope of the claims which follow.

I claim:

1. A contra-angle head for a dental handpiece comprising a rigid tubular housing member elongated axially to provide an alley open at a first end for receiving a drive shaft and having at the second end a chamber with an access opening through a side of said housing member for receiving a dental tool rotatable on a tool axis that is transverse to said housing axis, a latch member in the form of a thin-walled tubular shell slidingly enclosing a portion of said housing member including said second end and being movable relative to said housing member, said latch member having a two-part aperture in its wall overlying said access opening of said tool chamber, said two-part aperture having a first part which is large enough to allow a tool to pass into and out of said access opening, and a second part which is an elongated relatively narrow extension from said first part and has a dimension that is smaller than said access opening for retaining a tool in said chamber, retaining means for keeping said latch member on said housing member and operative to restrict motion of said latch member relative to said housing member between a first limit in which said first part of said aperture is in register with said access opening, and a second limit in which said second part of said aperture overlies said access opening.

2. A contra-angle head according to claim 1 in which said latch member has a closed end around said second end of said housing member.

3. A contra-angle head according to claim 1 in which said closed end of said latch member is a dome-shaped shell.

4. A contra-angle head according to claim 1 in which the second end of said housing member is closed across the axis of said housing member.

5. A contra-angle head according to claim 1 in which said housing member has a rigid wall transverse to said housing axis separating said tool chamber from said shaft alley, and means in said transverse wall for supporting driving gears positioned in said chamber to drive a dental tool when the latter is held in said chamber by said latch member.

6. A contra-angle head according to claim 5 in which said driving gears are coupled to the end of a drive shaft extending along said axis within said shaft alley to said transverse wall.

7. A contra-angle head according to claim 1 in which said two-part aperture in the latch member comprises a substantially round hole and a slotted opening of smaller width extending from it in a circumferential direction around said housing axis, and the latch member is movable around the housing axis relative to the housing member, to locate one or the other of said two parts of said aperture over said access opening.

8. A contra-angle head according to claim 1 in which said two-part opening in the latch member comprises a substantially round hole and a slotted opening of smaller width extending from it in a direction along the housing axis, and the latch member is movable parallel to the housing axis relative to the housing member, to locate one or the other of said two parts of said aperture over said access opening.

* * * * *